US005155365A

United States Patent [19]
Cann et al.

[11] Patent Number: 5,155,365
[45] Date of Patent: Oct. 13, 1992

[54] EMISSION-TRANSMISSION IMAGING SYSTEM USING SINGLE ENERGY AND DUAL ENERGY TRANSMISSION AND RADIONUCLIDE EMISSION DATA

[75] Inventors: Christopher E. Cann, San Francisco; Bruce H. Hasegawa, So. San Francisco; Eric L. Gingold, all of Oakland, Calif.

[73] Assignee: The Regents of the University of California, Oakland, Calif.

[21] Appl. No.: 549,890

[22] Filed: Jul. 9, 1990

[51] Int. Cl.$^5$ .................... G01T 1/164; G01T 1/166
[52] U.S. Cl. ................. 250/363.02; 250/363.04; 378/5
[58] Field of Search .................. 378/4, 5, 156; 250/363.03, 363.04, 370.06

[56] References Cited

U.S. PATENT DOCUMENTS

| | | | |
|---|---|---|---|
| 3,914,607 | 10/1975 | Cho et al. | 250/308 |
| 4,029,963 | 6/1977 | Alvarez et al. | 378/5 |
| 4,578,803 | 3/1986 | Macovski | 378/156 |

FOREIGN PATENT DOCUMENTS

| | | | |
|---|---|---|---|
| 92974 | 6/1983 | Japan | 250/363.04 |
| 9100048 | 1/1991 | PCT Int'l Appl. | 250/363.04 |
| 1405819 | 6/1988 | U.S.S.R. | 378/4 |

OTHER PUBLICATIONS

Park et al, "Use of Simultaneous Transmission-Emission Scanning in the Diagnosis of Pericardial Effusion", *J. Nucl. Med.* (USA), 13(6), Jun. 1972, pp. 347–348.

Walter W. Peppler, "Combined Transmission-Emission Scanning Using Dual-Photon Absorptiometry", Ph. D. Thesis, for The University of Wisconsin, 1981.

David E. Kuhl, et al. "Transmission Scanning: A Useful Adjunct to Conventional Emission Scanning for Accurately Keying Isotope Deposition to Radiographic Anatomy[1]", *Transmission Scanning*, vol. 87, pp. 278–284, Aug. 1966.

Russell C. Briggs, et al. "Combined Emission-Transmission Scanning of the Skelton[1]", *Work in Progress*, vol. 90, pp. 348–350, Feb. 1968.

S. H. Cohn, et al. "A Whole-Body Counter With an Invariant Response to Radionuclide Distribution and Body Size", *Phys. Med. Biol.*, 1969, vol. 14, No. 4, pp. 645–658.

P. Tothill, et al. "Quantitative Profile Scanning for the Measurement of Organ Radioactivity", *Phys. Med. Biol.*, 1971, vol. 16, No. 4, pp. 625–626.

Acts of 1972 Scientific Program: Technologists' Scientific Sessions Presented at 19th Annual SNM Meeting, Abstracts: Presented Orally, "Combined Transmission-Emission Scanning in Chest Disease", b Dolores Alfieri, et al. vol. 13, No. 11, and "Transmission Scanning as and Aid to the Interpretation of Routine Emission Scans", by B. R. Westerman, et al. vol. 10 No. 6.

T. F. Budinger, et al. "Three-Dimensional Reconstruction in Nuclear Medicine Emission Imaging", *IEEE*

(List continued on next page.)

Primary Examiner—Carolyn E. Fields
Attorney, Agent, or Firm—Townsend and Townsend

[57] ABSTRACT

Radionuclide emission imaging is improved by correcting emission transmission data for attenuation along calculated path lengths and through calculated basis material. Single or dual energy projector data can be simultaneously obtained with radionuclide emission data to improve localization of radionuclide uptake. Dual energy x-ray projection techniques are used to calculate the path lengths and basis material (bone, tissue, fat). The radionuclide emission data and the transmitted x-ray data are simultaneously obtained using an energy selective photon detector whereby problems of misregistration are overcome. The dual-energy x-ray projection data are utilized to determine material-specific properties and are recombined into an effectively monoenergetic image, eliminating inaccuracies in material property estimation due to beam hardening. Use of a single instrument for simultaneous data collection also reduces technician time and floor space in a hospital.

15 Claims, 5 Drawing Sheets

OTHER PUBLICATIONS

*Transactions on Nuclear Science*, vol. NS-21, Jun. 1974.
Yutaka Suzuki, et al. "Whole Body Transmission-Emission Scanning with Whole Body Camera*", *Whole Body Transmission-Emission Scanning*, vol. 125, No. 4, pp. 978-980, Dec. 1975.

O. Nalcioglu, et al. "Dual Energy Attenuation Correction for Single Photon Emission Computed Tomography (SPECT)", *IEEE Transactions on Nuclear Science*, vol. NS-31, No. 1, Feb. 1984.

Dale L. Bailey, et al. "Improved SPECT Using Simultaneous Emission and Transmission Tomography", *The Journal of Nuclear, Medicine*, vol. 28, No. 5, pp. 844-851, May 1987.

Kenya Murase, et al. "A comparative study of attenuation correction algorithms in single photon emission computed tomography (SPECT)", *European Journal of Nuclear Medicine*, (1987) 13:55-62.

*Scan Diagnostic Imaging, The Business Biweekly of Medical Imaging*, vol. 2, No. 18, Sep. 28, 1988, pp. 7-8.

David N. Levin, et al. "Retrospective Geometric Correlation of MR, CT, and PET Images[1]", *Radiology*, vol. 169, No. 3, pp. 817-823, 1988.

C. J. Thompson, "Simultaneous Transmission and Emission Scans in Position Tomography", Presented at the IEEE Nuclear Science Symposium Orlando, Fla.: Nov. 9, 1988, Submitted to the IEEE Transactions on Nuclear Science (Feb. 1989).

Chan Hee Park, et al. "Use of Simultaneous Transmission-Emission Scanning in the Diagnosis of Pericardial Effusion", *Journal of Nuclear Medicine*, vol. 13, No. 6, pp. 347-348.

Product Literature—Imagine... 4 pages, M&SE Polyscan, Medical & Scientific Enterprises, Inc., Sudbury, Mass.

EMISSION-TRANSMISSION IMAGING SYSTEM USING SINGLE ENERGY AND DUAL ENERGY TRANSMISSION AND RADIONUCLIDE EMISSION DATA

This invention was made by Government support under Grant No. 1PO1DK-39964 awarded by the National Institute of Health. The Government has certain rights in the invention.

BACKGROUND OF THE INVENTION

This invention relates generally to x-ray transmission and radionuclide emission imaging systems. In a primary application the invention relates to a diagnostic imaging system where dual-energy x-ray transmission data are used to derive material properties of the object imaged, which properties are then used directly to correct radionuclide emission data obtained simultaneously from the same object using the same imaging system.

Emission radionuclide imaging is a well-established technique for localization of lesions in diagnostic radiology and nuclear medicine. Briefly, a compound labelled with a radionuclide or a radionuclide itself is injected into a subject. The radiolabelled material concentrates in an organ or lesion of interest, or can show a concentration defect. At a prescribed time following injection, the pattern of concentration of the radiolabelled material is imaged by a rectilinear scanner, gamma camera, single photon emission computed tomography (SPECT) system or positron emission tomography (PET) system. The imaging procedure requires a means to define the vector path along which the emitted gamma-ray travels before striking the detector of the imaging system. In the first three systems a collimator (typically made of lead or other high-atomic number material is interposed between the object and the detector to define the gamma ray path; in PET the unique characteristics of positron annihilation radiation are coupled with electronic circuitry to define the vector path. In all cases, the only information obtained when a gamma-ray strikes the detector is the fact that the photon originated somewhere within the object along the vector path projected back from the detector. For projection imaging systems, a two-dimensional image is formed with the intensity of each picture element, or pixel, proportional to the number of photons striking the detector at that position. In SPECT and PET, the vector paths are determined for multiple projection positions, or views, of the object, and cross-sectional or tomographic images are reconstructed of the object using standard algorithms. Again, the intensity assigned to each vector path is proportional to the number of photons striking the detector originating along the path, and the intensity of each pixel in the reconstructed image is related to these vector path intensities obtained at multiple views.

Both for projection and CT radionuclide imaging it is desireable to obtain absolute values for radionuclide concentrations (or radionuclide uptake) at each point in the image. Attenuation of the emitted photons within the object, before they reach the detector, is a function of the energy of the photons and the exact composition of the material through which the photon vector path passes to reach the detector. Photons emitted deeper within the object have a higher probability of attenuation than photons emitted near the surface. In addition, the composition of the material (in terms of effective atomic number, Z, and electron density) affects the attenuation, with more attenuation if the path passes through high Z or high density regions. Thus, in order to calculate absolute uptake or concentration of a radionuclide in a region of an object it is required that the path length of each type of material or tissue (or effective Z and electron density path lengths) be known for each vector. Attenuation corrections for emitted photons are made from this knowledge, allowing accurate concentration values to be obtained.

Prior art in this field involves two approaches. The first approach uses conventional projection or CT images to estimate the material composition of the object, from which attenuation corrections can be estimated. This involves obtaining a conventional image, mapping the radionuclide distribution onto the conventional image, generating estimated material path lengths along the emission vector paths, and correcting the observed radionuclide distribution based on these path lengths. There are two fundamental limitations in this approach. First the conventional and radionuclide images are obtained sequentially using different instruments, generally in different rooms and often on different days. These factors lead to significant problems in misregistration of the conventional and radionuclide image data sets. While 3-D image matching algorithms have been applied to this problem, their inability to solve the problem has kept them from routine use. Only limited success is obtained in objects of relatively time-invariant composition such as the head, and the method is essentially useless in objects such as the chest or abdomen where motion is continuous. Secondly, conventional CT or projection images suffer from inaccuracies in determined material properties due to beam hardening and scattering among other effects. Therefore, the attenuation corrections applied to the radionuclide data for photons of often very different energy than the x-ray data are only estimates.

The second approach known in prior art is the use of a radionuclide transmission source to obtain total path length attenuation measurements, then to use these measurements to estimate attenuation corrections for the emitted photons from the administered radionuclide. Budinger and Gullberg, "Three-Dimensional Reconstruction in Nuclear Science," *IEEE Transactions on Nuclear Science*, June 1974, have suggested the use of multiple radionuclide photon energies to obtain material-selective path length data, and Peppler, "Combined Transmission-Emission Scanning Using Dual-Photon Absorptiometry,"Ph. D. Thesis, University of Wisconsin, 1981, has used sequential measurements, using two radionuclide energies to obtain data about bone and soft-tissue path lengths followed by acquisition of emission data which was then corrected by the transmission measurements. Some of these prior approaches use simultaneous or near simultaneous acquisition of transmission and emission data while others use sequential acquisition. However, all have the fundamental limitation that the use of a radionuclide transmission source to determine effective material path lengths limits the accuracy of these measurements due to statistical noise in the transmitted photon intensity measurements.

Material-selective imaging using x-ray sources has been described by Alvarez and Macovski in U.S. Pat. No. 4,029,963. This method or modification thereof can be used to determine effective material path lengths using two sequentially or simultaneously-acquired data sets at two different effective photon energies. Once the object being imaged is decomposed into a basis set of two properties, a priori knowledge of the energy dependence of the basis properties can be used to reconstruct an image of the object at the exact energy of the radionuclide emission photon being imaged. From this image is derived exact attenuation corrections for the emitted photons.

The present invention overcomes the fundamental limitations of the prior art. Specifically, transmitted photons from an x-ray source are acquired simultaneously with emitted photons from the contained radionuclide source, using the same photon detector in an identical geometry, so all the problems of misregistration are overcome. The dual-energy x-ray projection data are solved exactly for material-specific properties and recombined into an effectively monoenergetic image, eliminating inaccuracies in material property estimation due to beam hardening. The high photon flux from the x-ray tube overcomes the accuracy limitation of radionuclide transmission sources.

SUMMARY OF THE INVENTION

A primary object of the invention is to provide a method and instrument to obtain accurate measurement of the uptake or distribution of a radionuclide within an object using dual-energy transmission x-ray determined material-specific attenuation properties to correct simultaneously-measured emission photon data.

Another object of the invention is improved localization of radionuclide emission using simultaneously acquired single energy or dual energy x-ray transmission.

In accordance with a feature of the invention, the accurate localized measurements so obtained can also be referenced to one or more of the materials in the object to obtain concentration information.

The invention includes a dual-energy x-ray source mounted opposite to a collimated photon-counting detector and associated pulse counting electronics capable of discriminating incident photons into at least three separate photon energy windows and counting at a rate of approximately one million counts per second per detector. An object of variable composition containing one or more radionuclide sources is interposed between the source and detector. Dual-energy x-ray transmission data along projections through the object are decomposed into two basis set projections of known energy dependence, then recombined into an effective monoenergetic projection at the energy (or energies) of the contained radionuclide source. Radionuclide emission data along the same projection vector as the dual-energy x-ray transmission data are acquired simultaneously using the third (or more) energy windows(s) of the detector. The monoenergetic and/or original decomposed basis set projections are used to correct the detected emission photon intensity for attenuation along the path vector, based on the measured material-selective attenuation path lengths. The corrected emission data are used to obtain the absolute quantity or concentration of the radionuclide along the projection path. A conventional projection or CT radionuclide image is then formed from the data projections superimposed on any of the images from the dual-energy x-ray data set. Alternatively, an image from a single energy x-ray data set simultaneously acquired with radionuclide emission data can be superimposed on a radionuclide data image to improve the localization of the radionuclide emission. The invention also has the clinical advantage of being a single instrument on which the equivalent of two conventional studies are done simultaneously, with attendant savings in technician time and floor space in the hospital.

The invention and objects and features thereof will be more readily apparent from the following detailed description and appended claims when taken with the drawings.

DETAILED DESCRIPTION OF ILLUSTRATIVE EMBODIMENTS

Figure 1A:
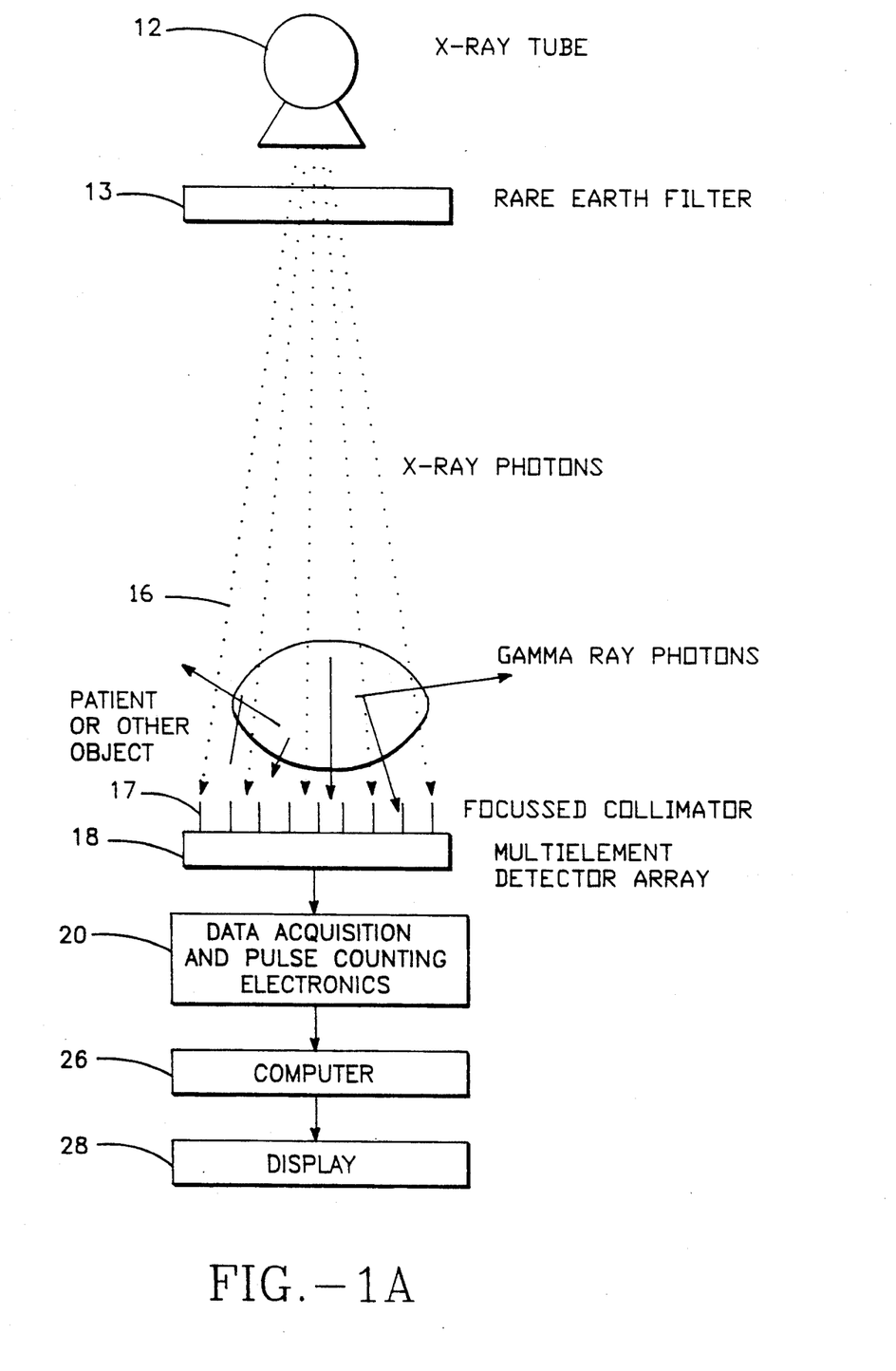
FIG. 1A is a schematic illustrating one embodiment of the invention.
Figure 1B:
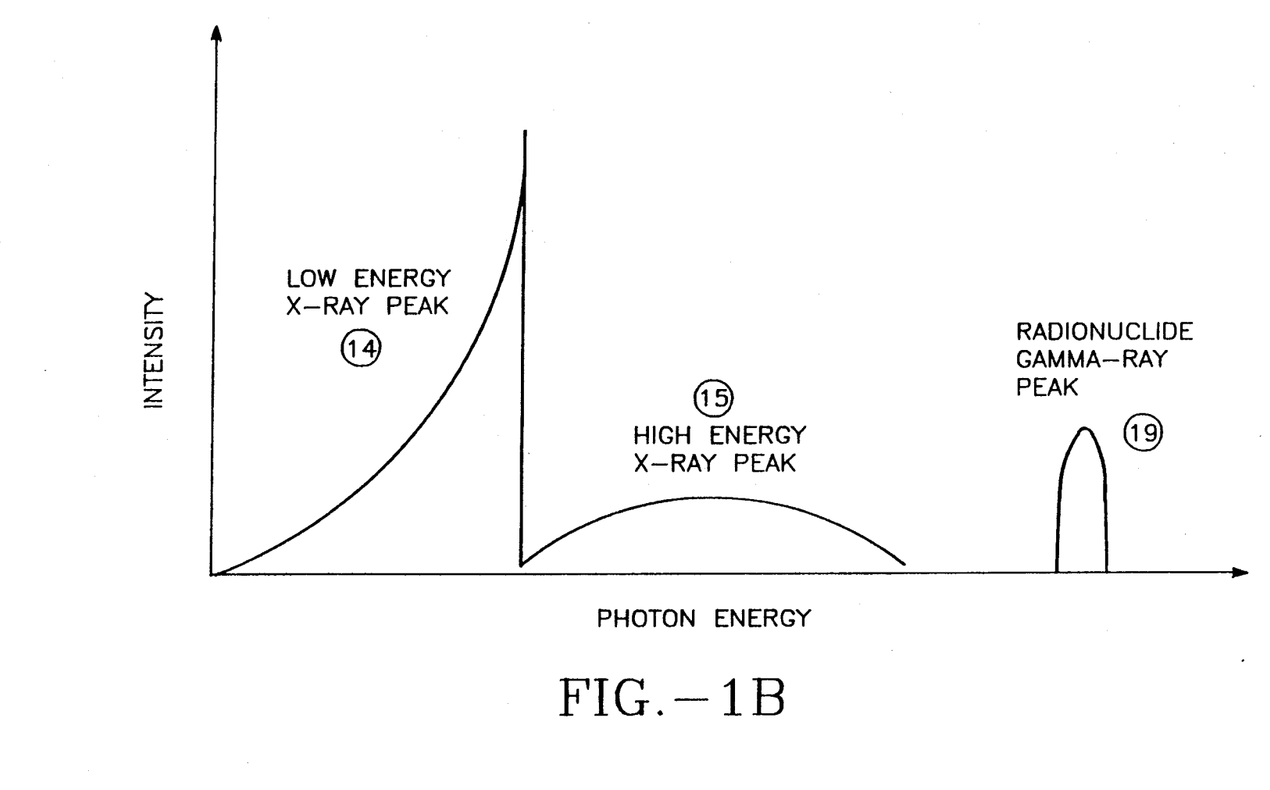
FIG. 1B shows a graph of a typical photon energy spectrum incident on the detector of FIG. 1A.
Figure 1C:
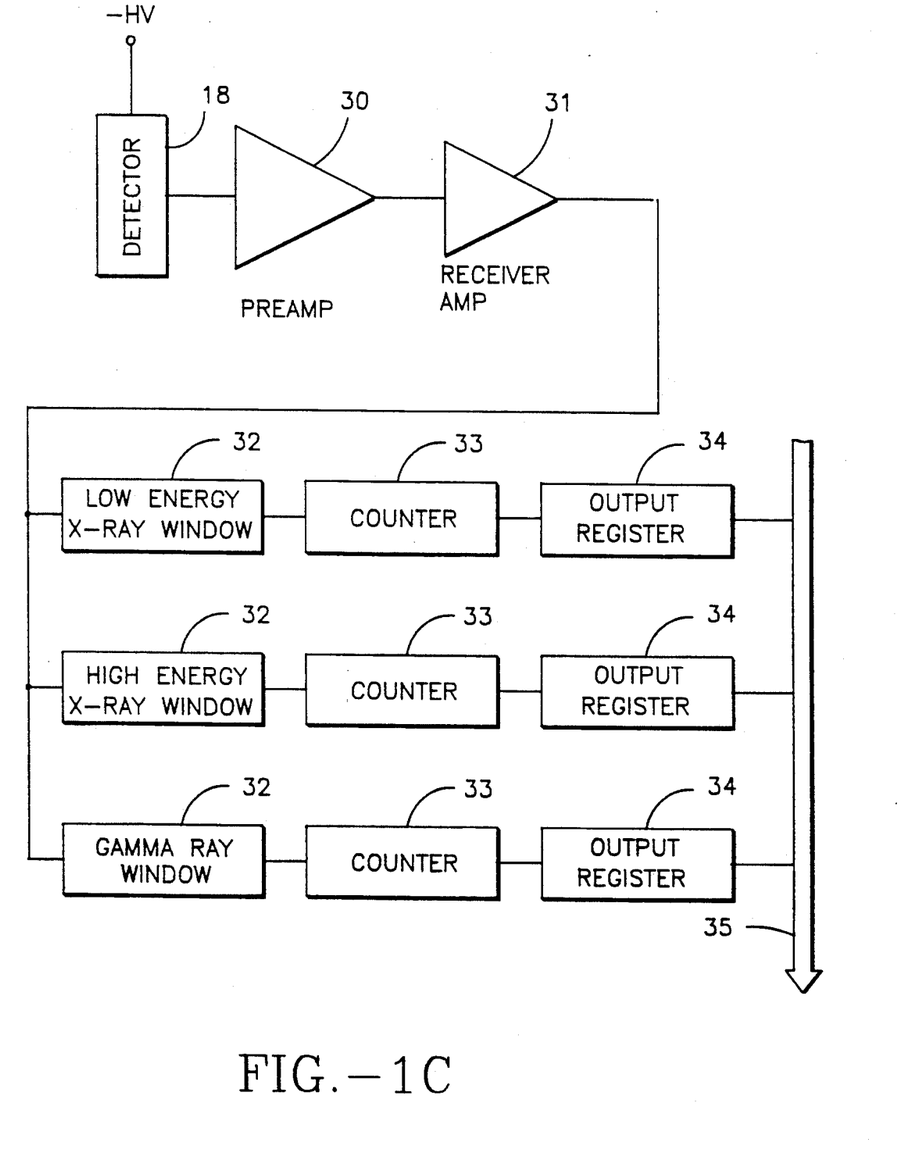
FIG. 1C shows a schematic of the detail of the data acquisition system of FIG. 1A.

An emission-transmission imaging system in accordance with one embodiment of the invention is illustrated in FIG. 1A. An x-ray tube 12 is mounted on a conventional gantry for either projection imaging or computed tomography. A rare earth filter 13 (e.g. samarium or gadolinium) is interposed between the x-ray tube and object 16 in order to produce a dual-energy x-ray spectrum incident on the object as shown by the low-energy 14 and high-energy 15 x-ray peaks in FIG. 1B. The low and high energy x-ray photons pass through the object 16, through a collimator 17 focussed at the x-ray source, and are incident on an energy-sensitive detector 18. The collimator has the dual function of rejecting scatter in x-ray transmission data and localizing the radionuclide emission path. The detector can consist of one or multiple elements and is also mounted (along with the collimator) on the gantry opposed to the x-ray tube. Photons emitted from a radionuclide(s) such as Xe-133 contained within the object are emitted isotropically with an energy 19 shown in FIG. 1B that is characteristic of the radionuclide. Those photons emitted in the direction of the detector pass through the collimator and are incident on the energy-sensitive detector. The detector must be capable of counting at very high counting rates with good energy resolution (in the range of 10 KeV at one million counts per second) in order to minimize crosstalk, pulse pileup and errors from scattered radiation. The high counting rate is necessary to produce low and high energy data sets of sufficient statistical accuracy in each projection to produce an accurate basis material decomposition. Such a detector is, for instance, high purity germanium, which is known in the art. Alternatively, other known high speed detectors such as cadmium telluride, lead iodide, and mercuric iodine can be used. The count from the multielement detector array 18 is passed to data acquisition and pulse counting electronics 20. As further illustrated in FIG. 1C, the electronics 20 includes preamplifiers 30 and amplifiers 31 which are optimized for these high counting rates and good energy resolution. The output voltage of the amplifiers is proportional to the photon energy spectrum incident on the detectors, and is sampled into three or more energy windows 32 using conventional high speed discriminator and logic chips. The data are counted at 33 and output through registers 34 and BUS 35 to a computer 26 and display 28.

Figure 2:
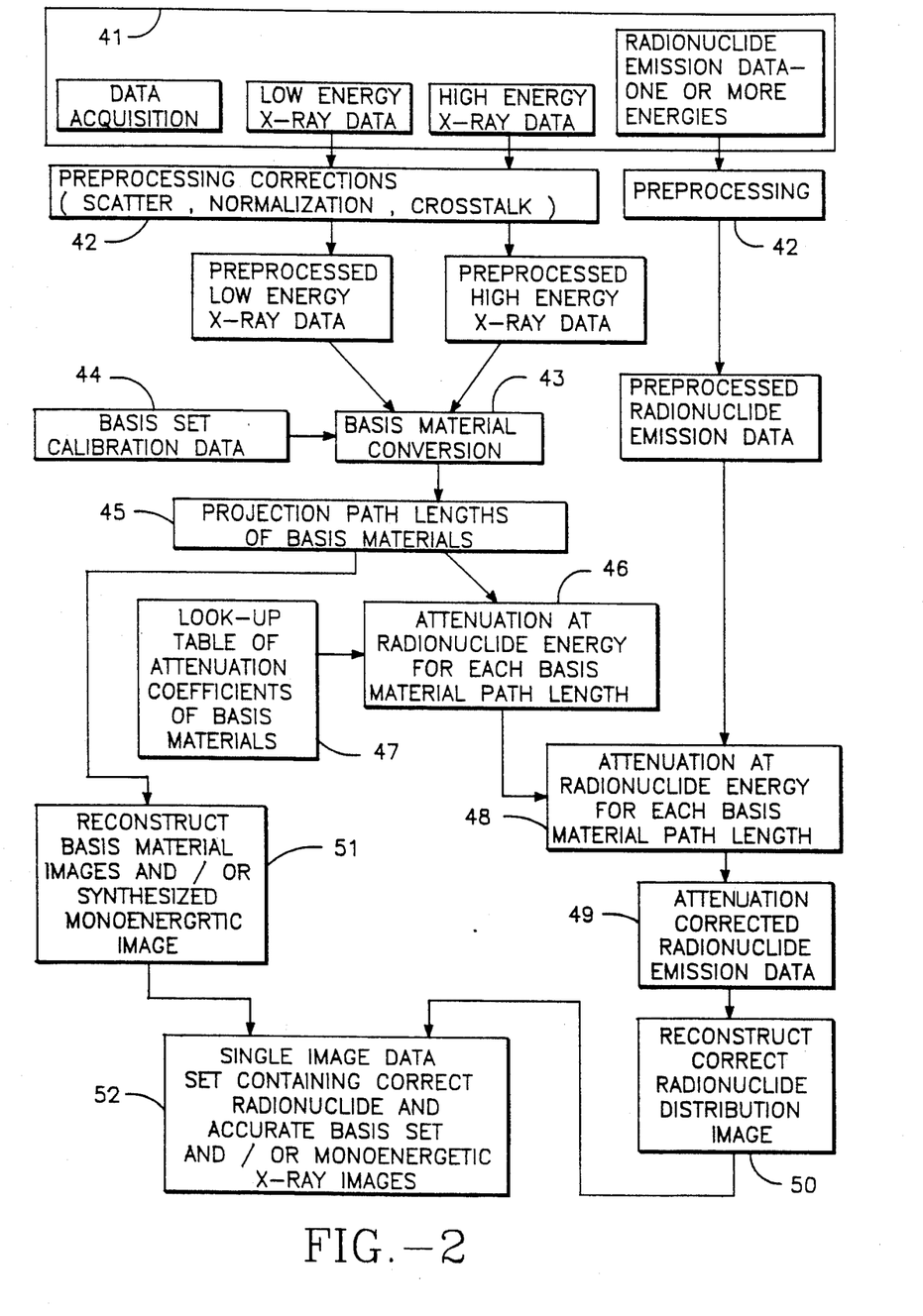
FIG. 2 illustrates the method required of practicing the invention.

Implementing the invention is best understood with reference to FIG. 2. Shown at 41 is simultaneous or near-simultaneous acquisition of transmitted x-ray photons at two effective energies along with emission gamma-ray photons from a point or distributed radionuclide source contained within the object as required to produce a data set free from limitations of prior art. Raw data (counts per second) in each data channel is preprocessed at 42 using conventional algorithms known in the field to reduce the errors due to scatter, normalization for multiple detectors, and crosstalk into the different energy windows due to scatter and pulse pileup. The preprocessed low and high energy x-ray data are converted to a new basis set of projections at 43 using calibration data 44 obtained for the system. This results in a new data set consisting of equivalent path lengths of the basis materials (e.g. bone, fat, tissue) at 45. Up to this point the method is similar to prior art as embodied in U.S. Pat. No. 4,029,963. Dual-energy x-ray data rather than radionuclide data are required to obtain accurate path lengths 45. The basis material equivalent path lengths 45 are then converted to attenuation coefficient line integrals 46 at the energy of the emitted photons from the radionuclide, using published values 47 for the energy dependence of the photon attenuation coefficients of the basis materials. The radionuclide emission data are then corrected at 48 for attenuation using a linear combination of the basis material attenuation data, resulting in the attenuation-corrected radionuclide emission data 49. Both radionuclide 50 and dual-energy x-ray transmission 51 images can then be reconstructed using conventional algorithms used in the field to obtain a single accurate data set 52 derived from the simultaneously-acquired dual-energy x-ray transmission data and radionuclide emission data. If more than one radionuclide energy window is used, the process can be repeated for this second or more data set(s).

The invention requires implementation of a well-known dual-energy material cancellation algorithm on instrumentation capable of producing data with low noise so the resulting corrections will be accurate. The algorithm used is as follows:

The dual-energy material-cancellation processing begins with the acquisition of calibration data from a dual-step-wedge with two dissimilar material (e.g. aluminum and acrylic) thicknesses increasing in orthogonal directions. The calibration data are used to relate the high-energy and low-energy radiographic measurements obtained during the patient scan, converted by a look-up table or interpolating polynomials, to equivalent aluminum and acrylic thicknesses $A_{al}$ and $A_{ac}$ or another such basis set such as calcium and water. For imaging lean soft-tissue (t), fat (f), and bone (b), the aluminum and acrylic equivalent projections then are linearly combined to yield equivalent tissue-cancelled (tc) or bone-cancelled (bc) projections $$A_{bc} = A_{ac} \cos\phi_{bc} + A_{al} \sin\phi_{bc}$$

and $A_{tc} = A_{ac}\cos\phi_{tc} + A_1\sin\phi_{tc}$ (E-1)

Where $\phi_{tc}$ and $\phi_{bc}$ are angles chosen to cancel the selected material. The bone-cancelled and tissue-cancelled data can be back-projected to obtain the fractional contributions of the bone-cancelled (fat and water) and tissue-cancelled (fat and bone) material $$f_{bc} = f_f + f_{tc} = f_b + f_f \qquad \text{(E-2)}$$

Since the sum of the constituent materials in any voxel must equal unity, $$f_f + f_t + f_b = 1 \qquad \text{(E-3)}$$

the equations can be solved to yield cross-sectional images of $f_f$, $f_t$, and $f_b$ showing the fractional distribution of fat, bone, and lean soft tissue in the reconstruction volume.

Synthesized monoenergetic images (i.e. corrected for beam-hardening errors) can be generated in one of two different ways. First, the constituent fractions of fat, tissue, and bone ($f_f$, $f_t$, $f_b$) can be combined with the linear attenuation coefficients at a given energy to calculate the linear attenuation coefficient at the energy for the composite material being imaged:

$$\mu(s,y;E) = f_f(x,y)\mu_f(E) + f_t(x,y)\mu_t(E) + f_b(x,y)\mu_b(E) \qquad \text{(E-4)}$$

where both the energy and spatial dependencies have been shown explicitly. Alternatively, the aluminum and acrylic equivalent projections $A_{al}$ and $A_{ac}$ can be back-projected to give the equivalent fractional contributions of aluminum and acrylic $a_{al}(x,y)$ and $a_{ac}(x,y)$ for the corresponding voxel in the image. These coefficients can be combined with the linear attenuation coefficients of aluminum and acrylic $$\mu(x,y;E) = a_{ac}(x,y)\mu_{ac}(E) + a_{al}(x,y)\mu_{al}(E) \qquad \text{(E-5)}$$

This image displays linear attenuation coefficients, similar to conventional (single-energy) tomograms, but different in that the synthesized monoenergetic image is devoid of any beam-hardening artifacts and that the display energy E can be chosen to be used for attenuation correction since they are obtained simultaneously and registered spatially with the radionuclide data.

Figure 3A:
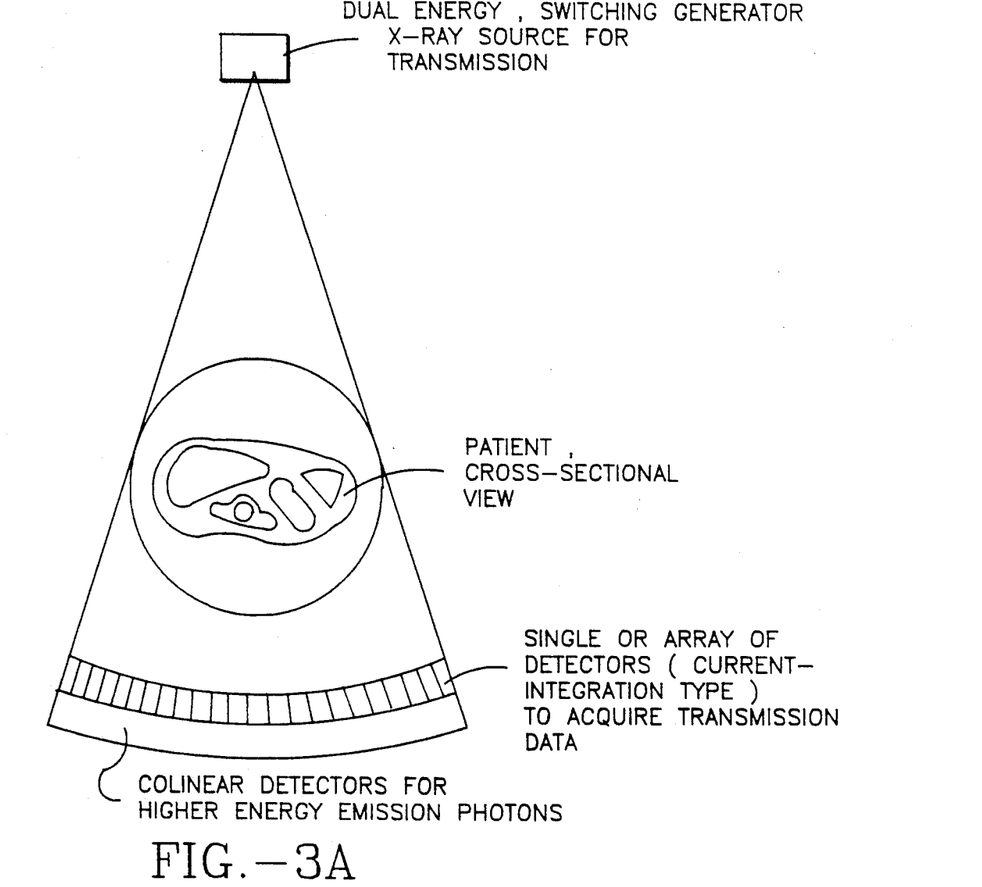
FIG. 3A and FIG. 3B illustrate an alternative embodiment of the invention.
Figure 3B:
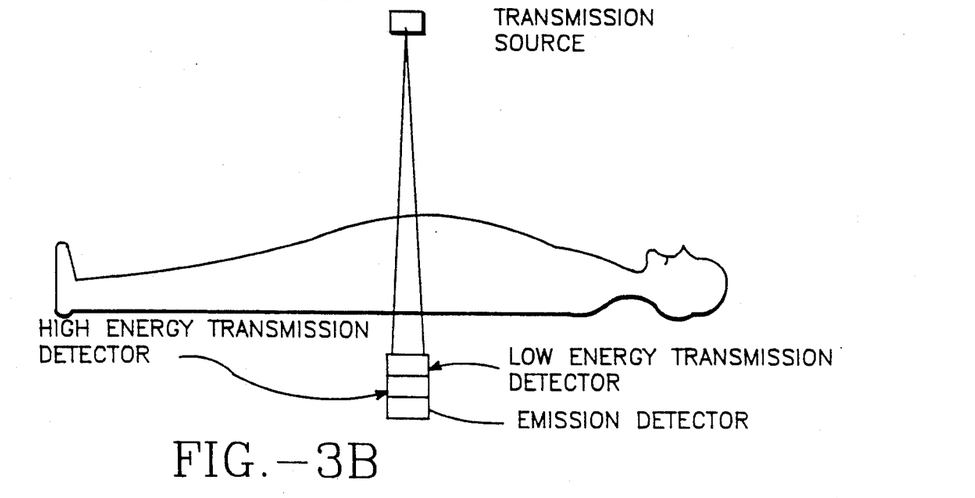

FIG. 3A shows one alternative embodiment of the invention where the low and high energy x-ray transmission and the radionuclide emission data are acquired nearly simultaneously using two stacked collinear energy selective detectors, one detector being current integrating for transmission data and one detector being pulse counting for emission data. Again, a dual energy x-ray source 60 is mounted opposite the detector array 62 with a patient 64 (shown in cross-section) therebetween. In this embodiment the x-ray source and the detector are switched. Alternatively, the detector array can include groups of three collinear detectors as illustrated in the side view of FIG. 3B. The three collinear detectors include a low energy detector 64, a high energy detector 65, and an emission detector 66 which selectively detect photons in the energy ranges shown in FIG. 1B, for example. The three detectors can be sodium iodide detectors and can be current integral type to acquire transmission data.

There has been described an improved imaging system in which x-ray transmission and radionuclide emission data are simultaneously obtained whereby tissue morphology obtained with dual energy x-ray CT or projection can be correlated with physiological measurements obtained using in vivo radiotracers. The simultaneous acquisition technique avoids the misregistration problem associated with using separate systems. In addition, the attenuation coefficient distribution derived from the x-ray CT or projection image can be used in the emission reconstruction method to compensate for attenuation to provide more accurate quantitative emission data. The resulting tissue separation capabilities of this system greatly aid tissue characterization and provide better attenuation correction for emission computed tomography.

While the invention has been described with reference to specific embodiments, the description is illustrative of the invention and is not to be construed as limiting the invention. Various modifications and applications may occur to those skilled in the art without departing from the true spirit and scope of the invention as defined by the appended claims.

What is claimed is:

1. An emission-transmission imaging system comprising
   a) an x-ray source for emitting a low energy x-ray spectrum and a high energy x-ray spectrum,
   b) detector means for simultaneously and selectively detecting photons corresponding to said low energy x-ray spectrum and said high energy x-ray spectrum and photons corresponding to radionuclide emission,
   c) means for positioning said x-ray source facing said detector means with an object positionable therebetween, said object having a radionuclide therein,
   d) data acquisition means connected with said detector means for receiving signals from said detector means representative of detected low energy x-ray spectrum photons, high energy x-ray spectrum photons, and radionuclide emission photons,
   e) computer means for receiving and processing said signals and producing image signals of distribution of a radionuclide in said object based on emission photon data as corrected for material-specific attenuation derived from dual energy x-ray transmission data, and
   f) display means responsive to said image signals.

2. The emission-transmission imaging system as defined by claim 1 wherein said x-ray source comprises an x-ray tube and a rare earth filter.

3. The emission-transmission imaging system as defined by claim 2 wherein said detector means comprises an array of multielement high speed detectors and said data acquisition means comprises a plurality of x-ray windows and counters.

4. The emission-transmission imaging system as defined by claim 3 wherein each detector element is selected from the group consisting of germanium, cadmium telluride, lead iodide, and mercuric iodide.

5. The emission-transmission imaging system as defined by claim 2 wherein said detector means comprises a plurality of stacked collinear detectors.

6. The emission-transmission imaging system as defined by claim 5 wherein said collinear detectors comprise sodium iodide.

7. The emission-transmission imaging system as defined by claim 6 wherein one collinear detector is current integrating and is responsive to a switched x-ray source, another detector is pulse counting and responsive to radionuclide emission.

8. A method of providing an improved radionuclide emission image comprising the steps of
   providing a multiple energy x-ray source,
   providing detector means for simultaneously and selectively detecting photons corresponding to multiple energies from said x-ray source and photons from radionuclide emission,
   positioning a body having a radionuclide therein between said source and said detector means,
   simultaneously detecting photons from said x-ray source and from said radionuclide and generating signals indicative thereof,
   determining path lengths for basic materials for photons from radionuclide emission based on data from detected photons from said x-ray source,
   correcting radionuclide emission data based on attenuation thereof through said path lengths, for said basis materials, and
   displaying a radionuclide emission image based on the corrected radionuclide data.

9. The method as defined by claim 8 wherein said basis materials are equivalent to soft tissue and bone.

10. The method as defined by claim 8 and further including the step of reconstructing a basis material image using signals from detected photons from said x-ray source.

11. The method as defined by claim 10 wherein said step of reconstructing a basis material image utilizes dual energy reconstruction techniques.

12. The method as defined by claim 11 wherein said dual energy reconstruction techniques include obtaining bone cancelled data and tissue cancelled data from which equivalent constituent fractions of tissue and bone are derived.

13. In radionuclide emission imaging, a method of correcting radionuclide emission data for an improved image comprising the steps of
    simultaneously and selectively obtaining radionuclide emission data from a body and multiple energy x-ray transmission data from x rays passed through said body,
    determining basis material path lengths from said multiple energy x-ray transmission data, and
    correcting said radionuclide emission data based on attenuation of radionuclide emission along said basis material path lengths.

14. The method as defined by claim 13 wherein dual energy reconstruction techniques are utilized to determine bone cancelled data and tissue cancelled data from which equivalent fractions of tissue and bone are derived.

15. The method as defined by claim 13 wherein said step of determining basis material path lengths includes dual energy CT reconstruction.

* * * * *